US012496227B2

(12) United States Patent
Soghadi

(10) Patent No.: US 12,496,227 B2
(45) Date of Patent: Dec. 16, 2025

(54) HYGIENIC DUAL-ENDED EAR-CLEANING SWAB WITH CONTINUOUS AIRFLOW PASSAGE AND SANITARY WRAPPING

(71) Applicant: Soheil Ighani Soghadi, Oceanside, CA (US)

(72) Inventor: Soheil Ighani Soghadi, Oceanside, CA (US)

( * ) Notice: Subject to any disclaimer, the term of this patent is extended or adjusted under 35 U.S.C. 154(b) by 0 days.

(21) Appl. No.: 18/606,486

(22) Filed: Mar. 15, 2024

(65) Prior Publication Data

US 2025/0288465 A1 Sep. 18, 2025

(51) Int. Cl.
*A61B 17/50* (2006.01)
*A61F 11/00* (2022.01)

(52) U.S. Cl.
CPC .................................. *A61F 11/006* (2013.01)

(58) Field of Classification Search
CPC ............................... A61F 11/006; A61F 13/38
See application file for complete search history.

(56) References Cited

U.S. PATENT DOCUMENTS

2015/0351968 A1* 12/2015 Shane .................... A61F 11/006 606/162
2018/0078421 A1* 3/2018 Trombley ............. A61F 11/006
2022/0054317 A1* 2/2022 Frandsen ................ A61F 13/38

* cited by examiner

*Primary Examiner* — Anh T Dang

(57) ABSTRACT

This disclosure describes systems, methods, and devices for a hygienic dual-ended ear-cleaning swab, innovatively designed to safely and effectively remove earwax. Central to its design is an elongated body featuring a continuous longitudinal hole which ensures uninterrupted airflow, extending through silicone tips at both ends. These tips are specifically shaped with a flared base to enhance cleaning efficiency and to prevent the inadvertent pushing of debris further into the ear canal. Adaptable to various ear sizes and inclusive of a water-absorbent variant for swimmers, the swab addresses the diverse needs of users. Constructed from durable, flexible materials and incorporating hypoallergenic properties, this ear-cleaning device offers a substantial improvement in personal hygiene care.

16 Claims, 4 Drawing Sheets

HYGIENIC DUAL-ENDED EAR-CLEANING SWAB WITH CONTINUOUS AIRFLOW PASSAGE AND SANITARY WRAPPING

TECHNICAL FIELD

This application relates generally to personal care and medical hygiene instruments. More specifically, this application relates to a hygienic dual-ended ear-cleaning swab designed for hygienic earwax removal.

BRIEF DESCRIPTION OF THE DRAWINGS

The drawings, when considered in connection with the following description, are presented for the purpose of facilitating an understanding of the subject matter sought to be protected.

DETAILED DESCRIPTION

Figure 1A:
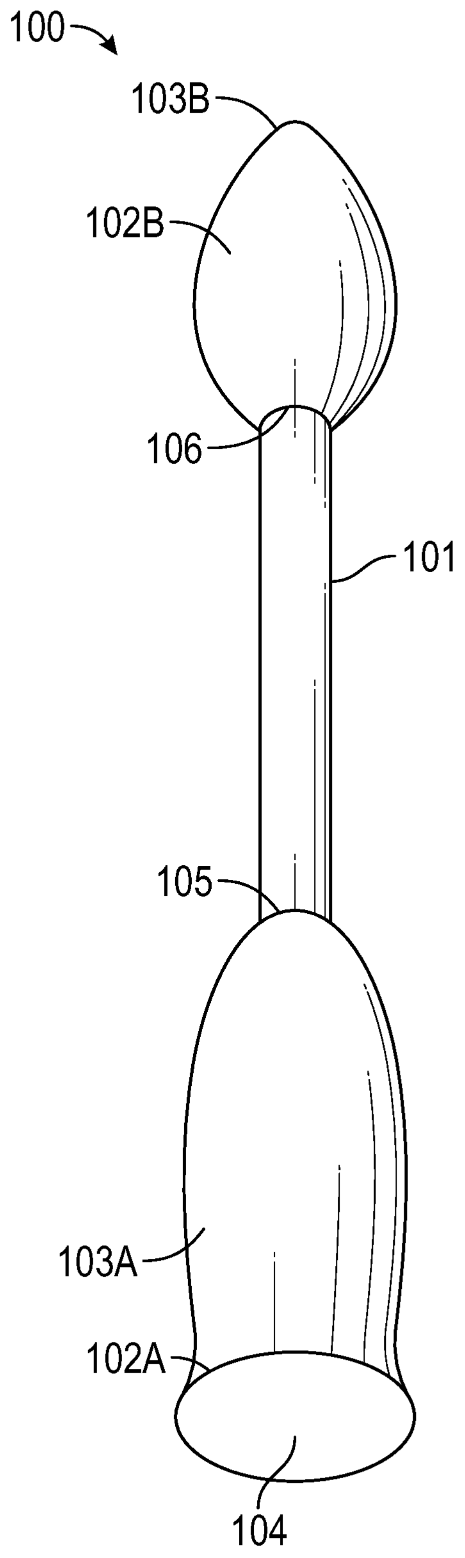
FIG. 1A shows an example of a dual-ended ear-cleaning swab positioned upright, featuring a central shaft, silicone tips at each end, and a continuous longitudinal hole.

While the present disclosure is described with reference to several illustrative embodiments and example devices described herein, it should be clear that the present disclosure should not be limited to such embodiments. Therefore, the description of the embodiments provided herein is illustrative of the present disclosure and should not limit the scope of the disclosure as claimed. In addition, this disclosure may be applied to other configurations and designs of personal hygiene devices.

Briefly described, a system and a method are disclosed including a hygienic dual-ended swab designed for personal care and medical hygiene applications. The swab incorporates a central shaft that includes a continuous longitudinal hole extending along the entire length of the swab body. The shaft terminates in silicone tips at both ends. These silicone tips are perforated and sheathed in a sanitary wrap. The wrap is strategically aligned with the continuous longitudinal hole of the central shaft, allowing for an uninterrupted air passage. This structural alignment is critical for the swab's function, as it not only facilitates the effective extraction of earwax and debris but also prevents the accidental pushing of such materials deeper into the ear canal. The swab is adaptable for various ear sizes and includes a variant with water-absorbent capabilities, catering to swimmers or other individuals in a wet environment.

In some embodiments, the swab's central shaft is fabricated from a durable yet flexible material, providing ease of use and comfort. The silicone tips are affixed to the shaft's ends using a medical-grade adhesive, ensuring a secure and hygienic bond. The sanitary wrap, which is perforated to align with the shaft's hole, is wrapped around the silicone tips, maintaining the passageway for airflow and cleaning efficacy.

In some embodiments, the swab is designed to be dual-ended, where each tip can be used interchangeably, thereby maximizing the utility of the swab. The silicone tips are tapered to facilitate easy entry into the ear canal, and the sanitary wrap provides a soft and absorbent surface for collecting debris.

In some embodiments, the swab is designed to be single-ended, encompassing all the features and functionalities of one end of the dual-ended model. This design ensures that the single-ended variant maintains the same efficacy and characteristics as its dual-ended counterpart. The single-ended swab includes a silicone tip, which is tapered for easy entry into the ear canal. It is also equipped with a sanitary wrap that offers a soft and absorbent surface, thereby effectively collecting debris during the ear-cleaning process, similar to the dual-ended version.

In some embodiments the swab includes a water-absorbent variant in which the sanitary wrap is made from a material with high moisture-wicking properties, making it particularly useful for swimmers or situations where moisture control is important.

In some embodiments the swab comprises a one-piece central shaft crafted from a durable yet flexible material, offering both structural integrity and user comfort during use. Diverging from other embodiments, this model of the swab does not feature separate silicone tips. Rather, the ends of the one-piece shaft, enveloped in sanitary wrap, are engineered to act as the cleaning tips. These built-in tips are integral to the shaft's uninterrupted structure and incorporate the continuous longitudinal hole characteristic of the swab, extending the entire length. To augment their functionality, the ends are specially treated to foster a soft, non-abrasive texture that is conducive to ear cleaning, while retaining enough firmness to facilitate the effective removal of earwax and debris. A gradient of flexibility may be imparted along the shaft, with the ends rendered more supple for safe and comfortable interaction with the ear's delicate tissues. The one-piece design eliminates the need for assembly and reduces the risk of detachment or wear at the junction points, thus ensuring a consistent and reliable cleaning experience. This embodiment of the swab is particularly beneficial for manufacturing simplicity and may offer advantages in terms of cost-effectiveness and ease of sterilization. The design remains in keeping with the invention's objectives to provide an effective, safe, and hygienic tool for personal care and medical hygiene.

In various embodiments, the elongated body of the swab is meticulously engineered to include a central shaft, which terminates into silicone tips at each end. A defining feature of this swab is its continuous longitudinal hole that extends throughout the length of the central shaft, seamlessly continuing into the silicone tips. This design feature not only ensures consistent airflow during the cleaning process but also aids in the effective removal of earwax and debris. The Silicon tips, each with a back end securely integrated or attached to the ends of the central shaft, are concluded with a flared base with pronounced edges. This flared base with pronounced edges not only helps to prevent the swab from being inserted too deeply into the ear canal but also contributes to a comfortable and secure fit. Each tip is meticulously wrapped in a sanitary material, keeping the interior passage open and unblocked.

In various embodiments, the central shaft of the ear-cleaning swab is constructed from a material chosen for its combination of flexibility and durability. This allows the user to safely and comfortably navigate the swab within the ear canal, making it an ideal tool for personal care and medical hygiene. The swab's structure is designed to hold up against the rigors of use without compromising on comfort or safety.

In various embodiments, especially tailored for those who lead an active lifestyle or are frequently in the water, such as swimmers or other individuals in a wet environment, the swab includes a version that has been enhanced with water-absorbent features. Both the sanitary wrap and the silicone tips themselves contain materials that excel in moisture management. This addition ensures that any moisture within the ear canal is efficiently absorbed, providing swimmers with a level of comfort and hygiene that is superior to traditional ear-cleaning solutions.

The evolution of ear cleaning devices, particularly cotton swabs, has been marked by a variety of applications, ranging from medical and surgical use to everyday personal care. These swabs are commonly used for tasks such as applying medication, removing makeup, cleaning small spaces, and most notably, for removing cerumen (earwax) from the ear canal. However, traditional cotton swabs, typically consisting of a plastic stem with cotton wads on both ends, have inherent limitations in effectively removing earwax, especially from the intricate cavities of the ear canal. Often, these swabs can push the wax deeper into the ear, potentially leading to ear damage, bacterial infections, and other health issues.

Despite various innovations in ear-cleaning tools, including designs aimed at safer ear insertion, enhanced cerumen removal, and ergonomic improvements for ease of use, there remains an unmet need for an ear-cleaning device that efficiently removes earwax while minimizing the risk of damaging the ear canal. This gap highlights the necessity for a new approach that addresses both the safety and effectiveness of earwax removal. The present invention is developed with the objective of overcoming the drawbacks of existing ear-cleaning devices, providing a novel solution that significantly enhances the safety and efficacy of the ear-cleaning process.

It is to be noted that directions, orientations, and other relative terms such as "front", "back", "top", "bottom", "left", "right", "inside", "outside", "interior", "exterior", "downward", "upward", "front-facing", "down-facing", "vertical", "horizontal", "diagonal", and the like are described with respect or relative to a distinguishing feature of the system or device body itself. For example, if the front part or surface of a system body or an object is identified in the description, then rear or back is defined as the part or surface opposite the front surface, left is defined as the left side when looking into the front surface, and so on. As long as directions are unambiguously identifiable based on the descriptions and figures, how the orientations are defined is immaterial.

FIG. 1A Shows an example of a dual-ended ear-cleaning swab body positioned upright, featuring a central shaft, silicone tips at each end, and a continuous longitudinal hole. Each Silicon tip is enclosed in a sanitary wrap.

In various embodiments, the swab body 100 includes a central shaft 101 having a first end 105, a second end 106, a continuous longitudinal hole 104, a first Silicone tip 102A and a corresponding section of a first sanitary wrap 103A, along with the part of the continuous longitudinal hole 104, a second Silicone tip 102B and a corresponding section of a second sanitary wrap 103B.

In various embodiments, the central Shaft 101 is a fundamental component of the dual-ended ear-cleaning swab, constituting the main structural element. It is typically cylindrical and serves as the backbone to which the other functional elements of the swab are attached or integrated, described below with respect to FIGS. 1A, 1B, and 1C.

In some embodiments, the material used for the central Shaft 101 is selected for its durability and flexibility. This ensures that the swab can withstand the pressures of use without breaking, while also being flexible enough to navigate the contours of the ear canal comfortably and safely.

In some embodiments, the Central Shaft 101 is designed to be slender and elongated, facilitating ease of handling by the user. It often has a smooth surface to prevent any irritation during use. A key functional feature of the central Shaft 101 is the continuous longitudinal hole 104, which runs through its center, described below with respect to FIGS. 1-C and 2. This hole is integral to the swab's operation, allowing for airflow and potentially aiding in the removal of earwax and debris by preventing the creation of a vacuum as the swab is used. The shaft's structure, combined with the hole, contributes to the swab's intended purpose of cleaning without pushing earwax further into the ear canal.

In some embodiments, at each end of the Central Shaft 101, there are tips, referred to in this context as first Silicone Tips 102A and second Silicon tip 102B. it some cases, these two tips may be either formed as part of the shaft or attached to it. These tips may be covered with a first Sanitary Wrap 103A and second sanitary wrap 103B to enhance the swab's ability to clean effectively and hygienically.

In some embodiments, the central shaft 101 of the ear-cleaning swab is a result of meticulous engineering, designed to optimize its functionality and user safety. It involves a careful selection of materials that provide the perfect balance of flexibility and durability, ensuring the shaft can navigate the ear canal's contours without damage or discomfort. Precision in dimensions is key, with the length, width, and diameter of the continuous longitudinal hole calculated to effectively reach and clean the ear canal while facilitating proper airflow. The integration of the shaft with the silicone tips is thoughtfully executed, ensuring a secure and hygienic connection essential for the swab's structural integrity. This includes the depth to which the shaft extends into the tips and the method of attachment (e.g., friction fit, adhesive). A secure and hygienic bond between the shaft and the tips is crucial for the overall integrity of the swab. Additionally, ergonomic considerations are made for comfortable and controlled use, and hygiene factors are meticulously addressed to reduce the risk of infections, making the shaft a crucial, well-conceived component of the swab.

Figure 1B:
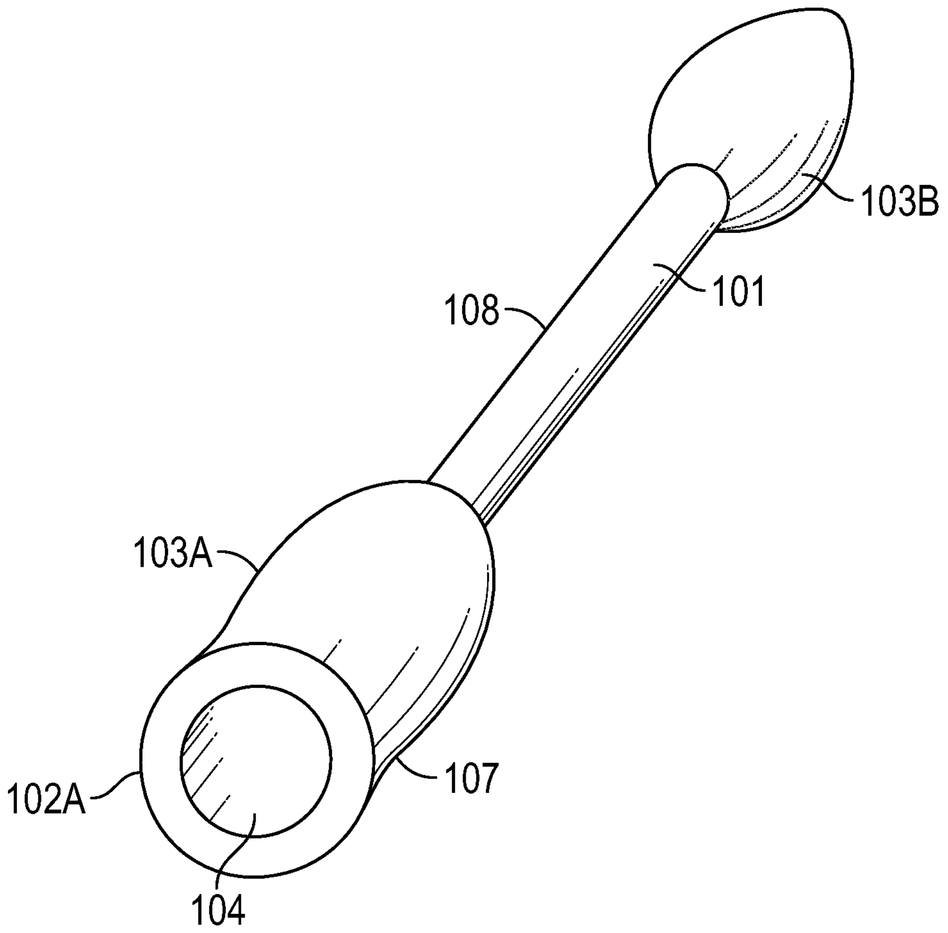
FIG. 1B shows the example close-up view of a dual-ended ear-cleaning swab body of FIG. 1A, showcasing one end of the device in greater detail, highlighting the central shaft which includes a visible segment of the continuous longitudinal hole.

FIG. 1B shows the example close-up view of a dual-ended ear-cleaning swab body of FIG. 1A, showcasing one end of the device in greater detail, highlighting the central shaft which includes a visible segment of the continuous longitudinal hole. This demonstrates that the passage extends into the silicone tip, specifically into Silicone tip 102A, and is encompassed by sanitary wrap 103A, with a similar configuration mirrored at the other end as sanitary wrap 103(B).

In various embodiments, the continuous longitudinal hole 104 of the ear-cleaning swab is a central feature of the device's design. The continuous longitudinal hole 104 is a through passage that runs along the entire length of the swab body 100. During the ear-cleaning process, the continuous longitudinal hole 104 allows air to flow through the swab. This prevents the creation of a vacuum or pressure buildup within the ear canal, which could potentially push earwax further in, rather than removing it. The continuous longitudinal hole 104 provides a channel that may assist in the removal of earwax and debris. As the swab is twisted or moved within the ear canal, earwax can collect around this opening rather than being compacted. The presence of the continuous longitudinal hole 104 ensures that the swab does not simply smear or redistribute earwax along the canal, which could happen with a solid-tipped swab.

In various embodiments, the first Silicon tip 102A includes a cylindrical body that has first Silicon tip back end 108 attached to the central shaft 101 and first Silicon tip front end 107 includes a flared base with pronounced edges, and the first sanitary wrap 103A and second sanitary wrap 103B. Silicone is a synthetic polymer known for its flexibility, resilience, and biocompatibility. It is soft enough to be gentle on sensitive skin and the delicate lining of the ear canal, reducing the risk of irritation or injury during use. Silicone's durability also ensures that the tips maintain their shape and structural integrity even with repeated use. The tips are shaped to conform to the ergonomic requirements of ear cleaning. They are typically rounded or contoured to facilitate safe and comfortable insertion into the ear canal. The silicone's texture usually has a non-slip quality that aids in the effective removal of earwax without causing discomfort.

In various embodiments, the first Silicone tip 102A and the second Silicone tip 102B feature perforations that align with the continuous longitudinal hole 104 in the Central Shaft 101. These perforations are crucial for maintaining the unobstructed passage through the swab allowing airflow and preventing the buildup of pressure that could push earwax further into the ear canal.

In various embodiments, the first Silicone tip 102A and the second Silicone tip 102B are further wrapped in the first sanitary wrap 103A and second sanitary wrap 103B to add absorbency and increase the efficacy of the swab. This covering not only aids in the removal of earwax and debris but also contributes to the overall hygienic quality of the ear-cleaning process.

In various embodiments, the first sanitary wrap 103A and second sanitary wrap 103B are made from a soft, absorbent material that can safely interact with skin and the delicate lining of the ear canal. The material is selected for its hypoallergenic properties and its ability to absorb earwax and other debris effectively.

In various embodiments, the first sanitary wrap 103A begins at the back end of the first Silicon tip 108 and extend over the entire length of the first Silicon tip 102A and stops just under the flared base with pronounced edges at the front end of the first Silicon tip 107. The second sanitary wrap 103B begins at the back end of the second Silicon tip 109 and extend over the entire length of the second Silicon tip 102B and stops just under the flared base with pronounced edges at the front end of the second Silicon tip 110. The first sanitary wrap 103A and the second sanitary wrap 103B at each end of the device, adheres to the first Silicone tip 102A and second Silicon tip 102B, respectively, with a medical-grade adhesive suitable for skin contact, ensuring that it stays in place during use. This adherence is crucial to prevent the wraps from unraveling or slipping during the ear-cleaning process.

Figure 1C:
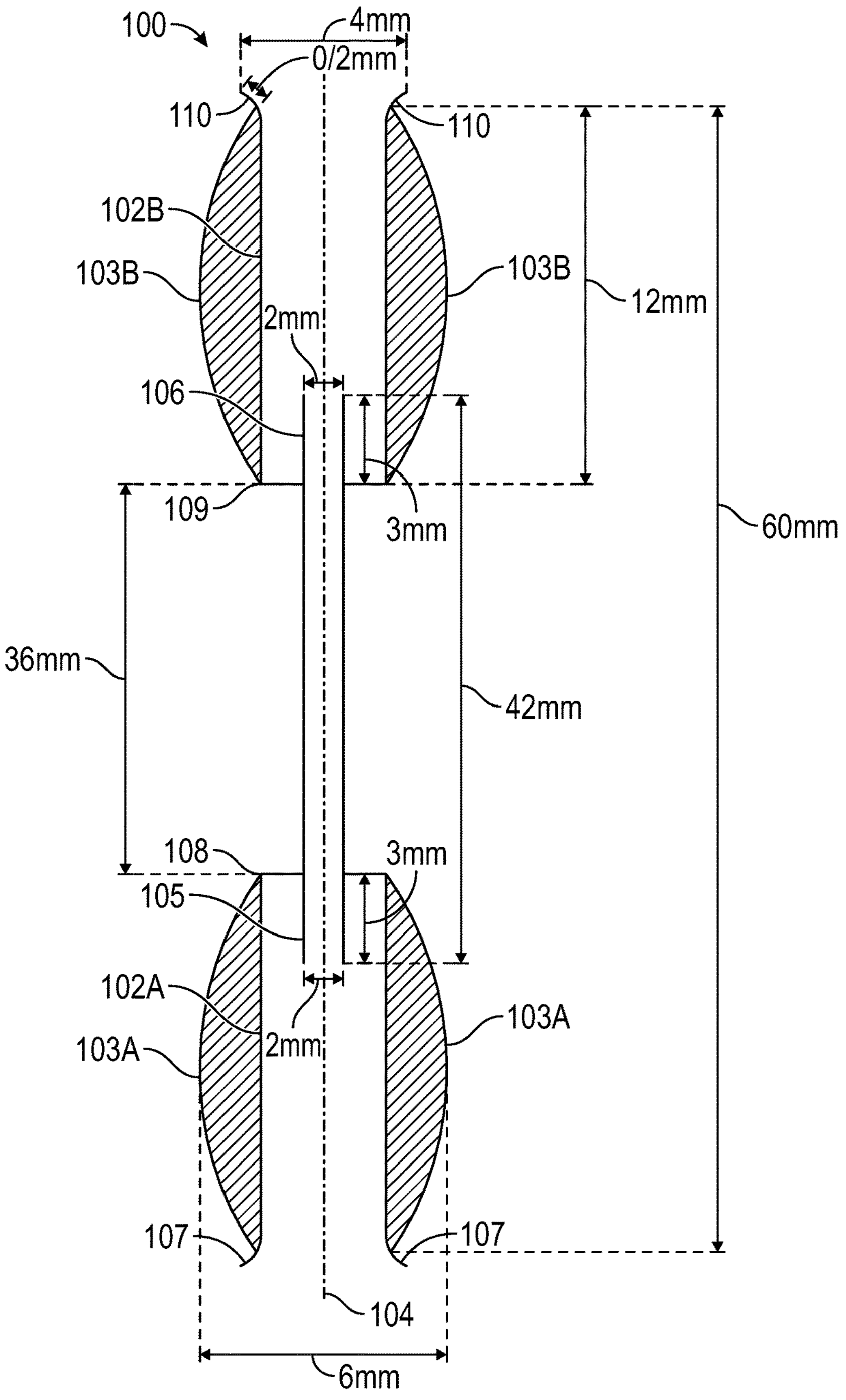
FIG. 1C shows the example main concept of the dual-ended ear-cleaning swab body of FIG. 1A, that incorporates the central shaft with the continuous longitudinal hole, that extends through the entire length of the swab, including through the perforated silicone tips. These tips are enveloped in sanitary wrapping at each end of the swab.

FIG. 1C shows the example main concept of the dual-ended ear-cleaning swab body of FIG. 1A, that incorporates the central shaft with the continuous longitudinal hole, that extends through the entire length of the swab, including through the perforated silicone tips. These tips are enveloped in sanitary wrapping at each end of the swab.

In various embodiments, the swab body 100 includes a central shaft 101 having a first end 105, a second end 106, a continuous longitudinal hole 104, a first Silicone tip 102A and a corresponding section of a first sanitary wrap 103A, along with the part of the continuous longitudinal hole 104, a second Silicone tip 102B and a corresponding section of a second sanitary wrap 103B.

In various embodiments, the hygienic dual-ended ear-cleaning swab body 100 features a central shaft 101 that is 2 mm in width and 42 mm in length. At each end of the central shaft 101, first end 105 and second end 106, the first Silicone tip 102A and the second Silicon tip 102B respectively are attached, and first Silicone tip 102A and second Silicon tip 102B along with their sanitary wraps 103A and 103B respectively, have a combined width of 6 mm. The first sanitary wrap 103A and the second sanitary wrap 103B are designed to encase the first Silicone tip 102A and the second Silicon tip 102B, providing a hygienic surface that comes into contact with the ear. The flared base with pronounced edges aids in securing the first sanitary wrap 103A around the first silicone tip 102A and the second sanitary wrap 103B around the second silicone tip 102B. The flared base with pronounced edges acts as a physical barrier on each tip, effectively preventing the wraps from slipping off.

When the back end of the first Silicone tip 108 and the back end of the second Silicone tip 109 are attached to the central shaft's first end 105 and central shaft' second end 106 respectively, the back end of the first Silicone tip 108 and the back end of the second Silicone tip 109 cover 3 mm of the central shaft's length at each end. This means that the central shaft's first end 105 extends 3 mm into the back end of the first Silicone tip 108 and the central shaft's second end 106 extends 3 mm into the back end of second Silicone tip 109, ensuring a secure fit and stability of the overall structure. The central shaft's narrower width of 2 mm gives the device a slim profile, while the 6 mm width of the first Silicone tip 102A and a corresponding section of the first sanitary wrap 103A, and the 6 mm width of the second Silicone tip 102B and a corresponding section of the second sanitary wrap 103B, ensures a comfortable fit within the ear canal.

It is important to understand that the dimensions, such as the 2 mm width of the central shaft 101 and the 6 mm width of the silicone tips 102A and 102B with their corresponding wraps 103A and 103B, are designed to fit a standard adult ear. However, when designing the device for different ear sizes, the dimensions can be adjusted accordingly. For example, for children or individuals with smaller ears, both the length and the width of the device, including the central shaft and silicon tips, might be reduced to ensure a comfortable fit. Similarly, for larger ears, the device can be made larger. The adaptability of the sizes allows the device to be customized for an individual's needs, enhancing the effectiveness and comfort of the ear-cleaning process. For swimmers, it is recommended that a more absorbent material is not only used for the sanitary wrap but may also be incorporated within the silicon tip itself. This is to ensure that any moisture that might be present in the ears of swimmers is effectively absorbed, thereby providing an added level of comfort and hygiene.

In various embodiments, the hygienic ear-cleaning swab 100 is meticulously designed with specific dimensions for comfortable handling and efficient ear cleaning. It has an overall body length of 60 mm, ideal for user handling during ear-cleaning activities. The central shaft 101, forming the core of the swab, measures approximately 42 mm in length and 2 mm in width. Notably, this shaft extends from its first end 105 and second end 106 by roughly 3 mm into the back ends 108 and 109 of the first and second silicone tips, 102A and 102B, respectively. This crucial design feature not only ensures a secure attachment of the first silicone tip back end 108 and the second silicone tip back end 109 to the central shaft's respective ends but also contributes to the total length of 60 mm of the swab, enhancing its effectiveness in reaching various depths within the ear canal. Each silicone tip, the first Silicone tip 102A and the second Silicone tip 102B, which are attached to the first end 105 and second end 106 of the central shaft respectively, measures about 12 mm in length. This dimension, in conjunction with the length and width of the central shaft (42 mm long and 2 mm wide), is integral in achieving the swab's overall length of 60 mm. The front ends 107 and 110 of each silicone tip are designed with a flared base, approximately 4 mm in diameter, and include a pronounced edge about 0.2 mm thick. This design is intended to enhance safety and comfort during use by preventing deep insertion into the ear canal. Moreover, the silicone tips, the first Silicon tip 102A and the second Silicon tip 102B, together with their respective sanitary wraps 103A and 103B, have a combined width of approximately 6 mm, a size carefully chosen to ensure effective cleaning while maintaining comfort within the ear canal.

Figure 2:
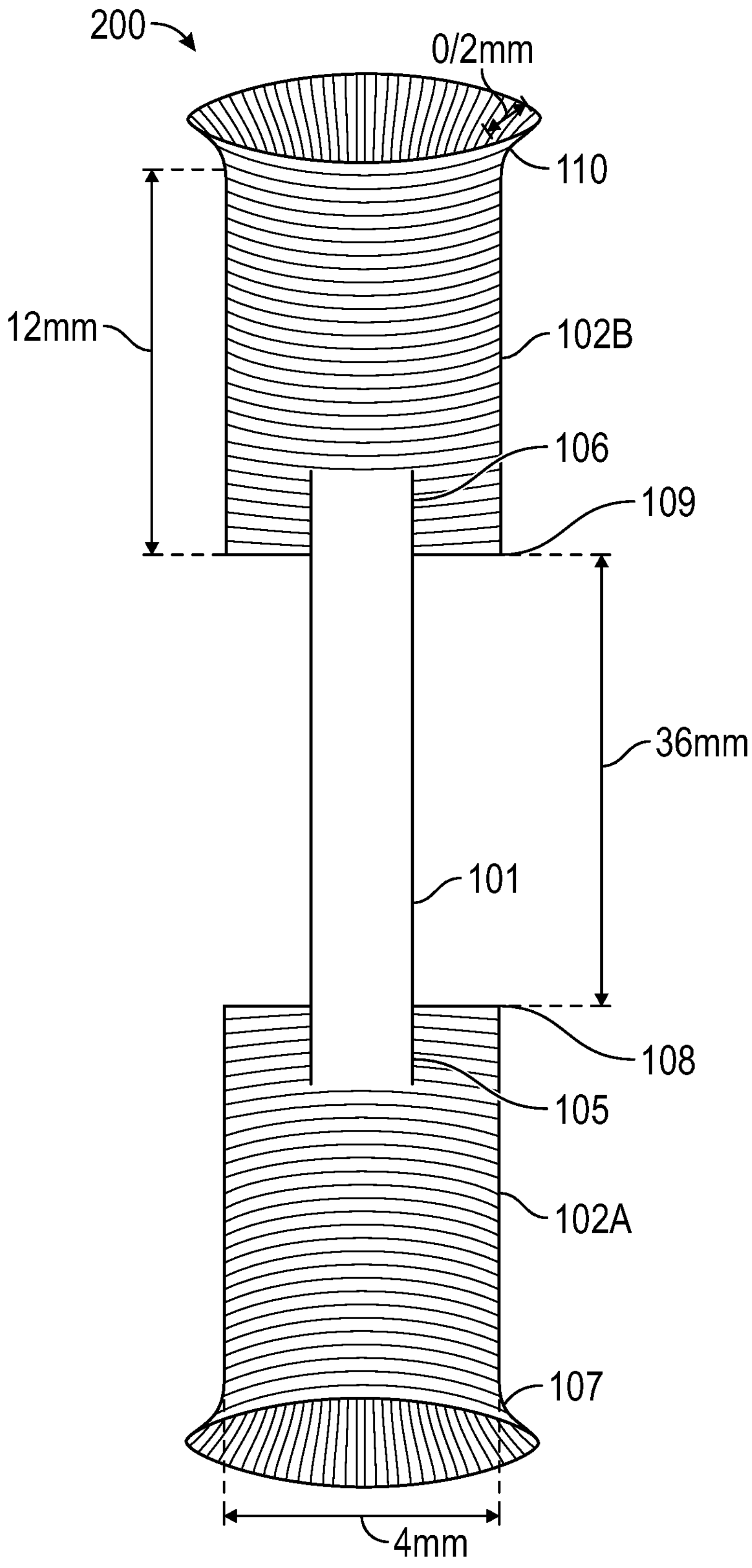
FIG. 2 shows an example of the detailed structure of the silicone tips of the ear-cleaning swab, presented without the sanitary wrapping.

FIG. 2 shows an example of the detailed structure of the silicone tips of the ear-cleaning swab, presented without the sanitary wrapping. It illustrates a cylindrical body for each tip, with the back end of each tip securely attached to the first end of the central shaft and similarly on the other side of the body. The front end of each silicone tip features a flared base with pronounced edges, also mirrored on each side of the body, emphasizing the symmetrical and functional design of the swab.

In various embodiments, the swab body 200 includes the first silicone tip 102A and the second silicone tip 102B at each end. Each of these silicone tips comprises a cylindrical body with back ends 108 and 109, which are respectively attached to the first end 105 and second end 106 of the central shaft. Additionally, the front end 107 of the first silicone tip and the front end 110 of the second silicone tip each include a flared base with pronounced edges.

In various embodiments, the back end of the first silicone tip 108 and the back end of the second Silicon tip 109 are specifically tailored to connect with the central shaft's first end 105 and central shaft's second end 106 respectively. This connection is intended to be tight and secure, employing methods such as a friction fit or the use of an appropriate adhesive. These methods ensure that the silicone tip remains firmly in place during the swab's operation, enhancing the safety and efficacy of the cleaning process.

In various embodiments, the front end of the first silicone tip 107 and the frond end of the second Silicon tip 110 include a flared base with pronounced edges. This means that it widens or spreads out in a shape that prevents the swab from being inserted too deeply into the ear canal, which could be harmful and also provides a comfortable and ergonomic interface with the outer part of the ear canal.

In various embodiments, each silicone tip, the first Silicone Tip 102A and the second Silicon tip 102B, extends approximately 12 mm from the point of attachment with the central shaft 101. At the front end of each silicone tip, the first Silicone tip front end 104 and the second Silicon tip front end 110, the flared base includes a pronounced edge with a thickness of approximately 0.2 mm. This edge design enhances the safety and comfort of the swab during use by preventing over-insertion into the ear canal. Additionally, the diameter of this flared base is about 4 mm, ensuring an ergonomic fit in the ear canal and contributing to the overall effectiveness of the swab.

It will be understood that unless explicitly stated or specified, the steps described in a process are not ordered and may not necessarily be performed or occur in the order described or depicted. For example, a step A in a process described prior to a step B in the same process, may actually be performed after step B. In other words, a collection of steps in a process for achieving an end-result may occur in any order unless otherwise stated.

Changes can be made to the claimed invention in light of the above Detailed Description. While the above description details certain embodiments of the invention and describes the best mode contemplated, no matter how detailed the above appears in text, the claimed invention can be practiced in many ways. Details of the system may vary considerably in its implementation details, while still being encompassed by the claimed invention disclosed herein.

Particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the claimed invention to the specific embodiments disclosed in the specification, unless the above Detailed Description section explicitly defines such terms. Accordingly, the actual scope of the claimed invention encompasses not only the disclosed embodiments, but also all equivalent ways of practicing or implementing the claimed invention.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." It is further understood that any phrase of the form "A/B" shall mean any one of "A", "B", "A or B", or "A and B". This construct includes the phrase "and/or" itself.

The above specification, examples, and data provide a complete description of the manufacture and use of the claimed invention. Since many embodiments of the claimed invention can be made without departing from the spirit and scope of the disclosure, the invention resides in the claims hereinafter appended. It is further understood that this disclosure is not limited to the disclosed embodiments but is intended to cover various arrangements included within the spirit and scope of the broadest interpretation so as to encompass all such modifications and equivalent arrangements.

What is claimed is:

1. A hygienic ear-cleaning swab with continuous airflow, comprising:

an elongate body with a continuous longitudinal hole traversing a length of the elongate body, wherein the elongate body includes:

a central shaft having a first end and a second end;

a first silicone tip, including:

a back end, wherein an inner section of the back end is integrally formed with or affixed to the first end of the central shaft, and a front end having a flared base with a pronounced edge;

a second silicone tip, comprising:

a back end, wherein an inner section of the back end is integrally formed with or affixed to the second end of the central shaft, and a front end having a flared base with a pronounced edge;

a first sanitary wrap enveloping the back end of the first silicone tip and extending over an entire length of the first silicone tip and stopping just under the flared base with the pronounced edge at the front end of the first silicone tip; and a second sanitary wrap enveloping the back end of the second silicone tip and extending over an entire length of the second silicone tip and stopping just under the flared base with the pronounced edge at the front end of the second silicone tip, wherein the first sanitary wrap and the second sanitary wrap enveloping the first silicone tip and the second silicone tip, respectively, in a way that the inner section of each silicone tip of the first silicone tip and the second silicone tip is shaped to continue a passage of the continuous longitudinal hole without an obstruction.

2. The hygienic ear-cleaning swab of claim 1, wherein the continuous longitudinal hole traverses the length of the central shaft and extends into both the first silicone tip and the second silicone tip attached at the first end of the central shaft and the second end of the central shaft, respectively, facilitating airflow during use and assisting in a removal of earwax and debris by preventing a formation of a vacuum within the ear canal.

3. The hygienic ear-cleaning swab of claim 1, wherein the central shaft is constructed from a flexible, durable material, allowing for comfortable and safe navigation within an ear canal while maintaining a structural integrity of the hygienic ear-cleaning swab during use.

4. The hygienic ear-cleaning swab of claim 1, wherein the inner section of each silicone tip of the first silicone tip and the second silicone tip is specifically shaped to continue the passage of the continuous longitudinal hole without the obstruction, ensuring a seamless airflow pathway throughout the hygienic ear-cleaning swab.

5. The hygienic ear-cleaning swab of claim 1, wherein the flared base with the pronounced edge at the front end of each silicone tip of the first silicone tip and the second silicone tip being configured to prevent over-insertion into the ear canal, provide a secure and ergonomic fit to enhance user comfort and safety, prevent slipping to ensure stable handling, and contribute to efficient earwax removal by creating an interface with an outer part of an ear canal.

6. The hygienic ear-cleaning swab of claim 1, wherein the first sanitary wrap and the second sanitary wrap of the hygienic ear-cleaning swab are made from a material with high moisture-wicking properties, and the first silicone tip and the second silicone tip are integrated with an internal water-absorbent material.

7. The hygienic ear-cleaning swab of claim 1, wherein the first sanitary wrap and the second sanitary wrap are hypoallergenic and designed to safely interact with skin and a delicate lining of the ear canal.

8. The hygienic ear-cleaning swab of claim 1, wherein the first silicone tip and the second silicone tip are attached to the central shaft using a medical-grade adhesive.

9. The hygienic ear-cleaning swab of claim 1, wherein the hygienic ear-cleaning swab is adaptable for different ear sizes, with dimensions adjustable to accommodate various user requirements.

10. The hygienic ear-cleaning swab of claim 1, wherein an overall length of the elongate body is approximately 60 mm.

11. The hygienic ear-cleaning swab of claim 1, wherein the central shaft has a total length of approximately 42 mm and a width of approximately 2 mm and extends approximately 3 mm from a point of attachment into the back end of each silicone tip of the first silicone tip and the second silicone tip.

12. The hygienic ear-cleaning swab of claim 1, wherein each silicone of the first silicone tip and the second silicone tip has a length of approximately 12 mm extending from a point of attachment with the central shaft, which has a total length of approximately 42 mm and a width of approximately 2 mm.

13. The hygienic ear-cleaning swab of claim 1, wherein the flared base at the front end of each silicone tip of the first silicone tip and the second silicone tip, having an approximate diameter of 4 mm, includes the pronounced edge with a thickness of approximately 0.2 mm, designed to enhance a safety and comfort of the hygienic ear-cleaning swab during ear-cleaning, by preventing over-insertion into the ear canal.

14. The hygienic ear-cleaning swab of claim 1, wherein the first silicone tip and the second silicone tip, along with the first sanitary wrap and the second sanitary wrap, have a combined width of approximately 6 mm.

15. The hygienic ear-cleaning swab with continuous air-flow of claim 1, wherein the first sanitary wrap and the second sanitary wrap are made from a material with hypo-allergenic properties and effective absorbency for earwax and other debris.

16. The hygienic ear-cleaning swab of claim 1, wherein the central shaft itself extends approximately 3 mm into the back end of each silicone tip of the first silicone tip and the second silicone tip, ensuring a secure fit and contributing to the total length of the hygienic ear-cleaning swab, which is approximately 60 mm, thus allowing for effective use within various depths of the ear canal.

* * * * *